United States Patent [19]

Berg

[11] Patent Number: 5,358,608
[45] Date of Patent: Oct. 25, 1994

[54] SEPARATION OF 1-PROPANOL FROM 2-BUTANOL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 181,795

[22] Filed: Jan. 18, 1994

[51] Int. Cl.5 .......................... B01D 3/40; C07C 29/84
[52] U.S. Cl. ........................................ 203/57; 203/60; 203/62; 203/65; 568/913; 568/918
[58] Field of Search ...................... 203/65, 57, 60, 62; 568/913, 918

[56] References Cited

U.S. PATENT DOCUMENTS

| | | | |
|---|---|---|---|
| 2,559,519 | 7/1951 | Smith et al. | 203/64 |
| 2,570,205 | 10/1951 | Carlson et al. | 203/58 |
| 2,575,243 | 11/1951 | Carlson et al. | 203/60 |
| 2,583,412 | 1/1952 | Carlson et al. | 203/65 |
| 4,715,933 | 12/1987 | Berg et al. | 203/60 |

*Primary Examiner*—Wilbur Bascomb, Jr.

[57] ABSTRACT

1-Propanol is difficult to separate from 2-butanol by conventional distillation or rectification because of the proximity of their boiling points. 1-Propanol can be readily separated from 2-butanol by extractive distillation. Effective agents are isobutyl acetate, isobornyl methyl acetate and ethyl butyrate.

1 Claim, No Drawings

SEPARATION OF 1-PROPANOL FROM 2-BUTANOL BY EXTRACTIVE DISTILLATION

FIELD OF THE INVENTION

This invention relates to a method for separating 1-propanol from 2-butanol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

There are a number of commercial processes which produce complex mixtures of oxygenated organic compounds, e.g. the Fischer-Tropsch process. In this mixture, a series of homologous alcohols are often produced. Two of the commonest alcohols in this mixture are 1-propanol and 2-butanol. 1-Propanol boils at 97.2° C. and 2-butanol at 99.5° C. The relative volatility between these two is 1.17 which makes it very difficult to separate them by conventional rectification.

Distillation would be an attractive method of effecting the separation of 1-propenol from 2-butanol if agents can be found that (1) will create a large apparent relative volatility between 1-propanol and 2-butanol and (2) are easy to recover from 1-propanol. Table 1 shows the relative volatility required to obtain 99% purity. With no agent, the relative volatility is 1.17 and 78 actual plates are required. With an agent giving a relative volatility of 1.55 only 28 plates are required.

TABLE 1

Theoretical and Actual Plates Required vs. Relatve Volatility for 1-Propanol - 2-Butanol Separation

| Relative Volatility | Theoretical Plates Required At Total Reflux, 99% Purity | Actual Plates Required 75% Efficiency |
| --- | --- | --- |
| 1.17 | 64 | 85 |
| 1.30 | 35 | 47 |
| 1.35 | 31 | 41 |
| 1.45 | 25 | 34 |
| 1.55 | 23 | 31 |

OBJECTIVE OF THE INVENTION

The object of this invention is to provide a process or method of extractive distillation that will enhance the relative volatility of 1-propanol from -2-butanol in their separation in a rectification column.

It is a further object of this invention to identify organic compound: which in addition to the above constraints, are stable, can be separate from 1-propanol and recycled to the extractive column with little decomposition.

SUMMARY OF THE INVENTION

The objects of this invention are to provide a process for separating 1-propanol from 2-butanol which entails the use of certain organic compounds as the agent in extractive distillation.

DETAILED DESCRIPTION OF THE INVENTION

TABLE 2

Effective Extractive Distillation Agents For Separating 1-Propanol From 2-Butanol

| Compounds | Relative Volatility |
| --- | --- |
| None | 1.17 |
| Phenol | 1.25 |
| a mixture of m-cresol and p-cresol. | 1.25 |
| 1-Nitropropane | 1.25 |
| 2-Nitropropane | 1.3 |
| Methyl salicylate | 1.3 |
| Ethyl salicylate | 1.25 |
| Isophorone | 1.25 |
| Ethyl butyrate | 1.55 |
| Propyl butyrate | 1.25 |
| n-Butyl acetate | 1.23 |
| Isobutyl acetate | 1.45 |
| Amyl acetate | 1.25 |
| Hexyl acetate | 1.25 |
| Ethyl n-valerate | 1.25 |
| Isoamyl formate | 1.25 |
| Methyl caproate | 1.3 |
| Isobutyl isobutyrate | 1.25 |
| Isobornyl methyl acetate | 1.45 |
| Cyclopentanone | 1.25 |

I have discovered that certain organic compounds will greatly improve the relative volatility of 1-propanol to 2-butanol and permit the separation of 1-propanol from 2-butanol by rectification when employed as the agent in extractive distillation. Table 2 lists the compounds that I have found to be effective. They are phenol, m-p-cresol, 1-nitropropane, 2-nitropropane, methyl salicylate, ethyl salicylate, isophorone, ethyl butyrate, propyl butyrate, n-butyl acetate, isobutyl acetate, amyl acetate, hexyl acetate, ethyl n-valerate, isoamyl formate, methyl caproate, isobutyl isobutyrate, isobornyl methyl acetate and cyclopentanone.

THE USEFULNESS OF THE INVENTION

The usefulness or utility of this invention can be demonstrated by referring to the data presented in Tables 1 and 2. All of the successful agents show that 1-propanol can be separated from 2-butanol by means of extractive distillation in a rectification column and that the ease of separation as measured by relative volatility is considerable.

WORKING EXAMPLES

Example 1

Sixty grams of 1-propanol, 40 grams of 2-butanol and 50 grams of isobornyl methyl acetate were charged to a vapor-liquid equilibrium still and refluxed for five hours. Analysis indicated a vapor composition of 67.4% 1-propanol, 32.6% 2-butanol; a liquid composition of 58.8% 1-propanol, 41.2% 2-butanol. This is a relative volatility of 1.45.

Example 2

A solution comprising 200 grams of 50% 1-propanol, 50% 2-butanol was placed in the stillpot of a 7.3 theoretical plate glass perforated plate rectification column. Isobutyl acetate as the extractive agent was pumped in continuously. The overhead temperature was 84° C. and the stillpot temperature was 110° C. After 1.5 hours of steady operation, overhead and stillpot samples were taken and analysed. The overhead composition was 52.1% 1-propanol, 47.9% 2-butanol and the stillpot composition was 19.4% 1-propanol, 80.6% 2-butanol. This gives a relative volatility of 1-propanol to 2-butanol of 1.23.

I claim:

1. A method for recovering 1-propanol from a mixture of 1-propanol and 2-butanol which comprises distilling a mixture of 1-propanol and 2-butanol in the presence of about one part by weight of an extractive agent per part of 1-propanol—2-butanol mixture, recovering the 1-propanol as overhead product and obtaining the 2-butanol and the extractive agent as bottoms product, wherein said extractive agent consists of one material selected from the group consisting of 1-nitropropane, 2-nitropropane, ethyl salicylate, isophorone, ethyl butyrate, propyl butyrate, n-butyl acetate, isobutyl acetate, amyl acetate, hexyl acetate, ethyl n-valerate, isoamyl formate, methyl caproate, isobutyl isobutyrate, isobornyl methyl acetate and cyclopentanone.

* * * * *